US008062884B2

(12) United States Patent
Sarofim

(10) Patent No.: US 8,062,884 B2
(45) Date of Patent: Nov. 22, 2011

(54) HANDLING KIT FOR ANALYZING A LIQUID SAMPLE BY NUCLEIC ACID AMPLIFICATION

(75) Inventor: Emad Sarofim, Hagendorn (CH)

(73) Assignee: Roche Molecular Systems, Inc., Pleasanton, CA (US)

( * ) Notice: Subject to any disclaimer, the term of this patent is extended or adjusted under 35 U.S.C. 154(b) by 136 days.

(21) Appl. No.: 12/373,518

(22) PCT Filed: Jul. 5, 2007

(86) PCT No.: PCT/EP2007/005954

§ 371 (c)(1),
(2), (4) Date: Jan. 12, 2009

(87) PCT Pub. No.: WO2008/006503

PCT Pub. Date: Jan. 17, 2008

(65) Prior Publication Data

US 2009/0317899 A1 Dec. 24, 2009

(30) Foreign Application Priority Data

Jul. 14, 2006 (EP) .................................... 06014684

(51) Int. Cl.
*C12M 1/34* (2006.01)

(52) U.S. Cl. ............... 435/288.5; 435/287.3; 435/288.1; 435/288.3; 435/288.4

(58) Field of Classification Search .................... 422/58; 436/164; 435/7.1, 287.3, 288.1, 288.3, 288.4, 435/288.5
See application file for complete search history.

(56) References Cited

U.S. PATENT DOCUMENTS

| | | | |
|---|---|---|---|
| 4,999,164 | A | 3/1991 | Puchinger et al. |
| 2004/0096358 | A1 | 5/2004 | Blankenstein et al. |
| 2004/0141880 | A1 | 7/2004 | Handler et al. |
| 2005/0148091 | A1 | 7/2005 | Kitaguchi et al. |

FOREIGN PATENT DOCUMENTS

| | | | |
|---|---|---|---|
| EP | 0264704 | A2 | 4/1988 |
| EP | 0264704 | A3 | 4/1988 |
| EP | 0264704 | B1 | 4/1988 |
| EP | 1643254 | A2 | 4/2006 |
| EP | 1643254 | A3 | 4/2006 |
| WO | EP2007005954 | | 10/2007 |

*Primary Examiner* — Nathan Bowers
*Assistant Examiner* — Gautam Prakash
(74) *Attorney, Agent, or Firm* — M. Reza Savari

(57) ABSTRACT

The invention refers to a handling kit for analyzing a liquid sample, especially by nucleic acid amplification, comprising a disposable sample holding and processing device (1) dimensioned for use in an apparatus for analyzing a liquid sample, and a sample transfer tip (12) for transferring liquid into the disposable device (1), the disposable device (1) having a sample preparation chamber (10) which has an outlet (9) and an insertion opening (16) which is adapted to receive the sample transfer tip (12), the insertion opening and the sample transfer tip (12) being dimensioned in such a way that inserting the sample transfer tip (12) into an insertion position in the sample preparation chamber (10) causes a tight seal between an outer wall (40) of the sample transfer tip (12) and an inner wall (41) of the sample preparation chamber (10), the disposable device (1) having a vent (31) for venting the sample preparation chamber (10).

15 Claims, 5 Drawing Sheets

HANDLING KIT FOR ANALYZING A LIQUID SAMPLE BY NUCLEIC ACID AMPLIFICATION

This application claims the benefit of priority under 35 U.S.C. §119 of EP Application 06014684.2 filed Jul. 14, 2006 the contents of which are hereby incorporated by reference.

The invention relates to a single use handling kit for analyzing a liquid sample, especially by nucleic acid amplification, comprising a disposable sample holding and processing device for being used in an apparatus for is analyzing a liquid sample, especially by nucleic acid amplification, and a sample transfer tip for transferring liquid into the disposable device, the disposable device having a sample preparation chamber which has an outlet and insertion opening which is adapted to receive the sample transfer tip.

A processing device for nucleic acid amplification is disclosed in U.S. Pat. No. 6,551,841 B1. The known device consists of a substrate of silicon or a polymeric material in which channels and chambers are formed. The substrate is covered by a cover made of glass or plastic which seals the channels and chambers between the substrate and the cover.

US 2004/0141880 A1 discloses transfer of liquids to a disposable device with a tip forming an air tight seal. The tip contacts only with its front end an inlet port of the disposable device and is successively used for the transfer of several liquids to the device via the same inlet port. This embodiment does not avoid the risk of contamination of the environment and of primary vessels of the liquids transferred.

Further processing devices are disclosed in US 2005/148091 A1, US 2004/096358 A1 and EP 1 643 254 A2.

In order to analyze large numbers of fluid samples by a nucleic acid amplification technique like polymerase chain reaction technique in a speedily and cost efficient way a disposable handling kit is needed which facilitates transferring a sample from a primary tube (e.g. sample storage or collection tube) into the processing device and facilitates a safe and contamination free execution of the analysis.

Upon this the following specific requirements have to be taken into account:

- The device should be suitable for performing a rather complex processing, e.g. forming the binding solution for the nucleic acid analysis, with enabling performing standard operation steps like addition of the sample, addition of reagents, incubation, closing of the chamber and pumping out of the chamber.
- The transfer of a sample into the disposable device with a disposable tip should be possible.
- When a sample, in particular a biological sample, is taken from a primary vessel by the tip there is a high risk that the outside of the tip is contaminated, at least to the extent at which the tip was immersed into the primary vessel or into the fluid comprised in the primary vessel. In order to avoid a contamination of the environment the tip should be possibly be immersed into a chamber of the device surrounding the tip at least to the extent at which it was immersed into the primary vessel or into the liquid in the primary vessel. Further, the tip should be kept in that in the chamber of the device after use of the tip upon using the device in order to avoid a contamination of the environment.
- In order to avoid a contamination of the tip before its use for transfer of a sample to the disposable device, e.g. by aerosols or drops, it is preferable when it can be kept for that purpose in the secured position in a chamber of the disposable device.
- In order to avoid spread, transmission and carry over of a contamination from a sample to a reagent container it should be possible to use separate ports for providing sample and for providing reagents to the disposable device.
- In order to avoid a contamination of the environment in mixing steps the chamber should be vented in a controlled manner A handling kit meeting these needs is provided according to the invention in that the insertion opening of the sample preparation chamber and the sample transfer tip being dimensioned in such a way that inserting the sample transfer tip into an insertion position in the sample preparation chamber causes a tight seal between an outer wall of the sample transfer tip and an inner wall of the sample preparation chamber, the disposable device also having a vent, in which preferably a filter material is placed, for venting the sample preparation chamber.

A tight seal between the sample transfer tip and the wall of the sample preparation chamber prevents contamination of the sample and facilitates transferring liquid into the disposable sample holding and processing device. Preferably the tight seal is distanced from the end of the sample transfer tip which is introduced into the sample preparation chamber by a distance which is at least 300%, preferably at least 50%, especially at least 75%, of the total length of the sample transfer tip. In this way the sample transfer tip reaches with the major part of its length into the device, i.e. into the sample preparation chamber, which results in a better and more precise positioning of the sample transfer tip as tilting of the sample transfer tip is reduced. A handling kit according to the invention is therefore readily suited for use with automated gripping devices which allow for fast processing and analyzing of sample liquid in an apparatus for analyzing sample by nucleic acid amplification.

The sample to be analyzed by the handling kit may be a body fluid, e.g. plasma, serum, urine, or any liquid gained by processing, mixing or other treatment of a body liquid. Other possibilities of samples include suspensions of biological material or any liquid containing an analyte.

Further details and advantages of the present invention are illustrated in the following based on an exemplary embodiment making reference to the attached drawings. The following is depicted in the figures.

Figure 1:
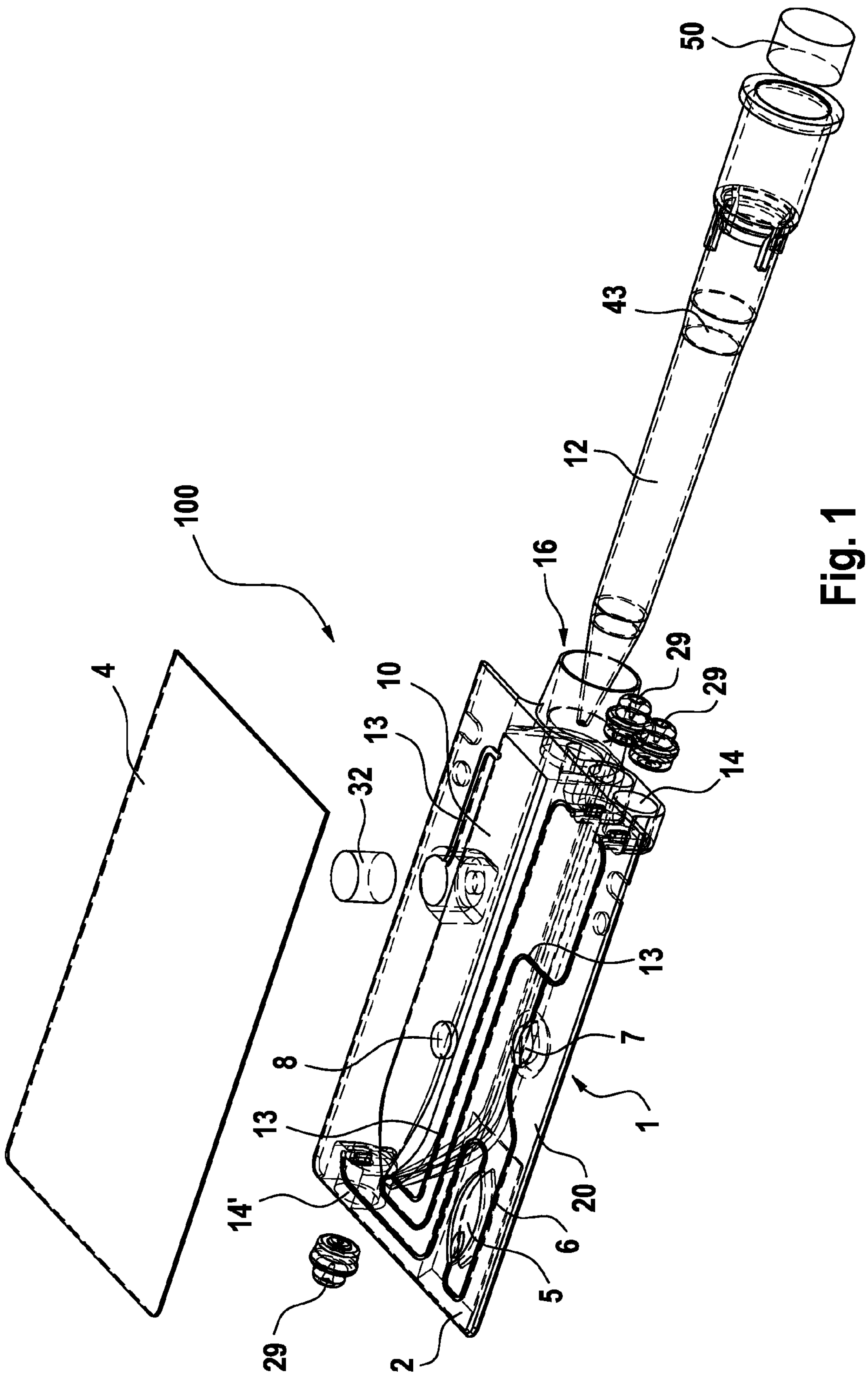
FIG. 1 shows an exploded view of an embodiment of a handling kit according to the invention comprising a disposable handling and processing device and a sample transfer tip.
Figure 2:
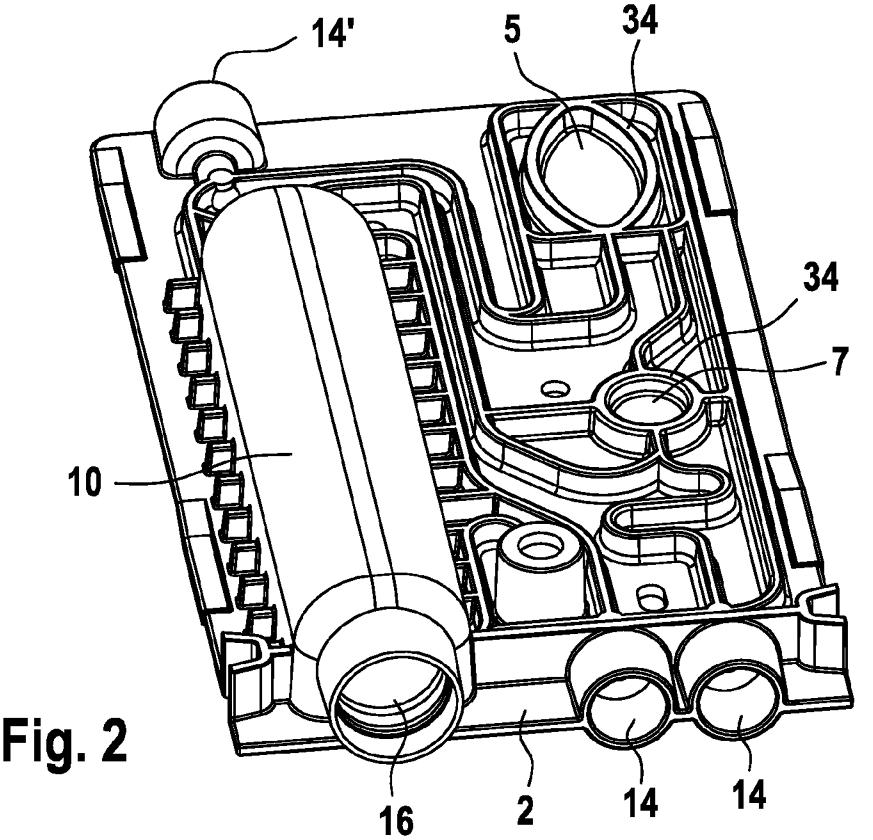
FIG. 2 shows a perspective view of the body of the disposable handling and processing device shown in FIG. 1.
Figure 3:
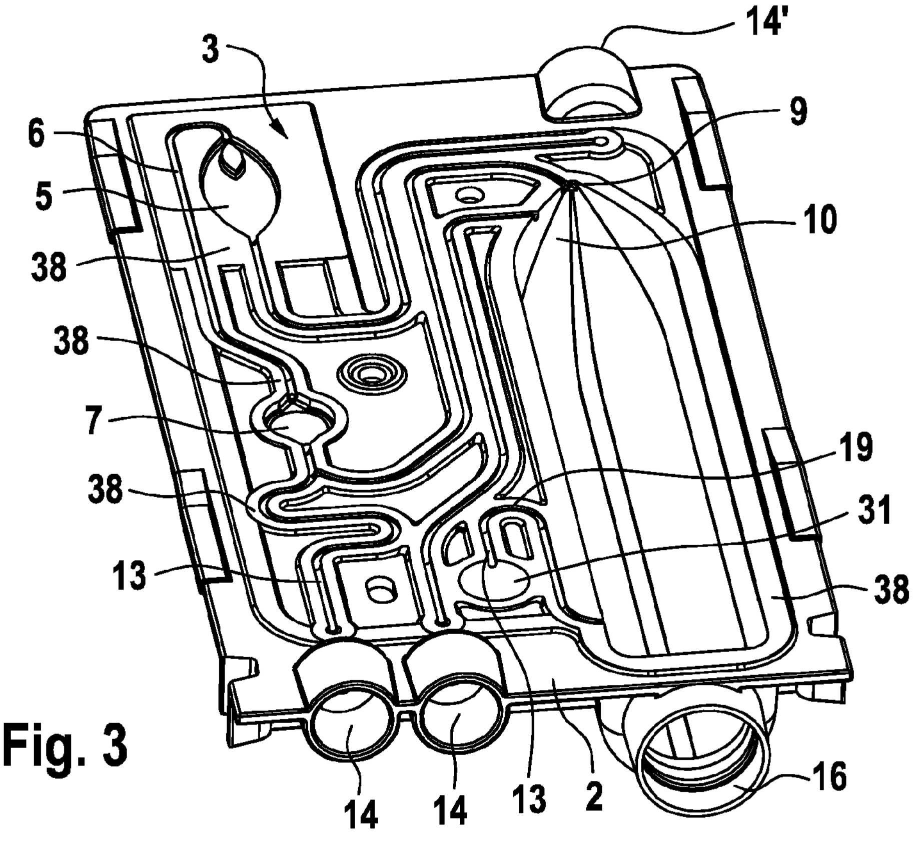
FIG. 3 shows another perspective view of the device body shown in FIG. 1.

FIG. 1 shows an exploded view of a handling kit 100 comprising a disposable handling and processing device 1 and a sample transfer tip 12. FIGS. 2 and 3 show the body 2 of the disposable sample holding and processing device 1, which is designed for being used in an apparatus for analyzing a liquid sample by nucleic acid amplification, especially by polymerase chain reaction technique, and therefore is dimensioned for insertion into such an apparatus. The device 1 comprises a device body 2 having a structured surface 3, which comprises grooves and depressions for channels and chambers, and a sealing cover 4 which covers the structured surface 3 thereby forming a wall of an amplification chamber 5 which is designed and intended for performing nucleic acid amplification and of an inlet channel 6 connected to the amplification chamber 5.

The device 1 also comprises a binding chamber 7 containing a solid phase adsorber 8, preferably a glass fiber fleece, for binding nucleic acids contained in the sample liquid. The device 1 also comprises a sample preparation chamber 10 with an insertion opening 16 adapted to receive the sample transfer tip 12. The sample preparation chamber 10 has an outlet 9 which is connected via a channel 13 to the binding chamber 7. The sample preparation chamber 10 has a volume of 50 μl to 20 ml, especially in the range of 200 μl to 10 ml, and is typically used for lysis of the sample material or, more generally, for a preparation step of the sample.

The various chambers 5, 7, 10 are connected by channels 13 with each other and/or to fluid interface ports 14, 14'. The binding chamber 7 has a volume of 5 μl to 500 μl, especially 10 μl to 100 μl. The amplification chamber 5 has a volume of 10 μl to 100 μl and is preferably at least as large as the volume of the binding chamber 7. The depth of the amplification chamber 5, the binding chamber 7, the channels 6 and 13 measured perpendicular to the sealing cover 4 is in the range of 50 μm to 2 mm, preferably 100 μm to 1 mm. The channels 6, 13 have a cross-section area of 0.01 $mm^2$ to 2 $mm^2$, especially 0.04 $mm^2$ to 0.5 $mm^2$.

Figure 4:
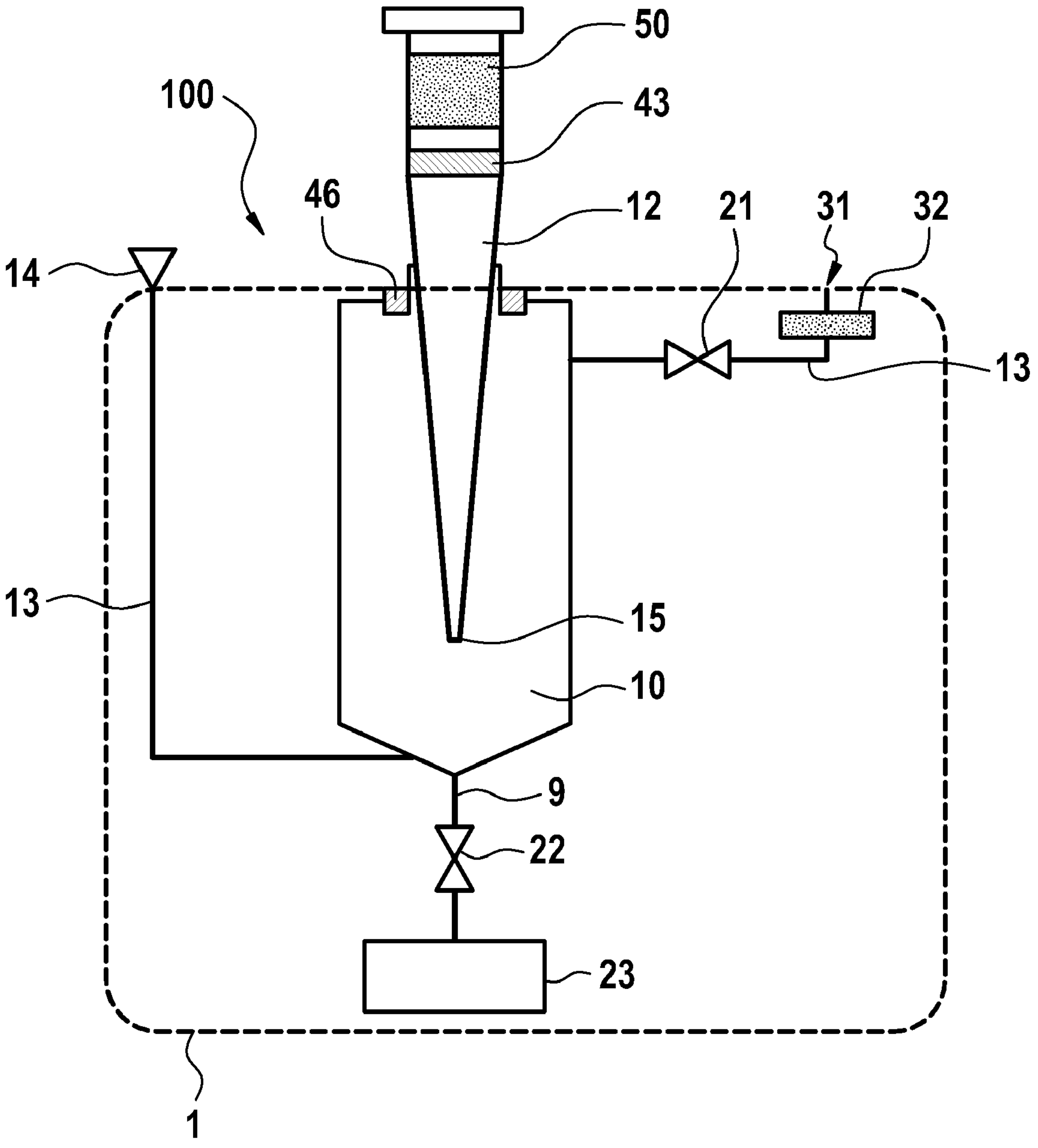
FIG. 4 shows a schematic sketch of the handling kit shown in FIG. 1.

FIG. 4 shows a schematic sketch of the function of the handling kit 100 comprising the device 1 and the sample transfer tip 12. Upon introduction of the tip 12 into the sample preparation chamber 10 the sealing area 43 of the tip and the sealing area 46 of the inner wall of chamber 10 form a tight seal. Reagents, e.g. for lysis, can be added to the sample preparation chamber 10 via the fluid interface port 14 and channel 13. A vent 31 which is closed by a filter 32 is also connected to the sample preparation chamber 10. The chamber 10 has an outlet 9 which leads to a fluidic system 23 which comprises the chamber 5 and 7 shown in FIGS. 1 to 3. Fluid control areas 21 and 22 can be used to close channels and thereby control the flow of gases or liquids. The fluid control areas may, for example, be closed by heat or pressure applied by an apparatus in which the handling kit 100 is used to analyze a sample.

The device body 2 comprises a sheet 20 made of a plastic material on which the structured surface 3 forming the channels 6, 13 and chambers 5, 7, 10 is arranged. The device body 2 is manufactured by injection molding. Suitable plastic materials, which are inert with respect to the sample liquid and to reagents, are for example polypropylene, polyethylene, polystyrene, polycarbonate and polymethylmethacrylate. Preferably a thermo-plastic material is used, especially polypropylene.

The structured surface 3 of the device body 2 is overlaid by the flat sealing cover 4 thereby forming a wall of the chambers 5, 7, 10 and channels 6, 13 of the device 1 and sealing them tight. The sealing cover 4 is a thin sheet material, for example a plastic foil, which touches the device body 2 in sealing areas 38. Preferably, the sealing cover 4 comprises more than one layer. In the example shown, it comprises a first layer (preferably touching the device body 2) made of a material which is inert with respect to the sample liquid and a second layer (wherein preferably the first layer is placed between the device body 2 and the second layer) which is made of a metal, preferably aluminum. The second layer is preferably thicker than the first layer.

The second layer provides an efficient way for transporting heat to the sample liquid or away from it. For heating or cooling of the sample the sealing cover 4 can be connected to a heating or cooling area of an analysis apparatus. Preferably, the thickness of the sealing cover 4 is as small as possible while still ensuring sufficient mechanical strength for reliably sealing the various chambers 5, 7, 10 of the device 1. The lower the thickness of the sealing cover 4 is the lower is its thermal capacity and the higher is the heat transfer rate. A low thermal capacity, a high heat transfer conductivity and high heat transfer rate are advantageous as they enable faster heating and cooling of the device 1, respectively of fluids therein.

Generally, the thickness of the sealing cover 4 should not exceed 1 mm, preferably be below 500 μm. In order to ensure sufficient mechanical strength for a reliable sealing of the chambers 5, 7, 10 and of the channels 6, 13 the thickness should be at least 50 μm. Especially advantageous is a thickness of 50 μm to 350 μm, especially of 60 μm to 200 μm.

Aluminum is particularly well suited as material for the second layer of the sealing cover 4 as it has a very low thermal capacity. Of course, other materials can also be used. The thickness of the second layer is preferably 20 μm to 400 μm, especially 20 μm to 200 μm.

As the function of the first layer is mainly to prevent contact between sample liquid and the second layer it is advantageous to provide the first layer with a thickness as small as possible while still ensuring a continuous layer. The thickness of the first layer should therefore be less than 300 μm, preferably less than 200 μm, especially less than 100 μm. Particularly preferred is a thickness of the first layer of 0.1 μm to 80 μm.

In the example shown the sealing cover 4 is a composite foil comprising the first layer and the second layer. The first layer can be laminated to the second layer or sprayed, painted or, for example, vapor deposited on the second layer. More layers can be added to the sealing cover 4, for example a coat of paint to protect the second layer. The overall heat transfer conductivity of the sealing cover 4 is at least 200 $^{-2}K^{-1}$, preferably at least 2000 $^{-2}K^{-1}$.

The sealing cover 4 can be fixed to the device body 2 by means of suitable bonding procedures, e.g. by thermal sealing or by use of an adhesive, e.g. a polyurethane or polymethylmethacrylate adhesive. Preferably, the sealing cover 4 is bonded using thermal bonding or welded, for example by ultrasonic welding or laser welding, to the device body 2. Welding is most feasible if the first layer of the sealing cover 4 consists of the same material as the device body 2, e.g. polypropylene. The sealing cover 4 and the device body 2 have positioning holes (not shown) which are used during manufacturing for precise positioning of the sealing cover 4 on the structured surface 3.

For providing reagents to, respectively for leading fluids out of the device 1, the device 1 has fluid interface ports 14, 14' which are connected to the channels 6, 13 or chambers 5, 7, 10 of the device 1. The fluid interface ports 14 are arranged on a small area side which adjoins both to a large area front, on which the sealing cover 4 is arranged, and a large area back of the device 1. In the example shown the interface ports 14, 14' comprise a cylindrical recess for a septum 29.

As FIG. 3 shows the fluid interface ports 14 are closed by septa 29 to prevent contamination of the device 1. The septa 29 are made of a suitable elastomere which can be pierced by a hollow needle, syringe or a similar device to deliver reagents or process gases into the device 1. The elastomere used for the septa 29 has a shore hardness in the range of 20 to 80 Shore A, preferably in the range of 30 to 60 Shore A. The insertion opening of the sample preparation chamber 10 is also arranged on that small area side. This arrangement enables processing of the device 1 in a vertical position in an analysis apparatus.

The fluid interface port 14' is arranged on the same side as the inlet ports 14 or on a different small area side which also adjoins both to the large area front and the large area back of the device 1. The fluid interface port 14' is connected directly to the amplification chamber 5 and can be used as an outlet port for removing gas and/or liquid from the device 1. Preferably the outlet interface port 14' is arranged on a small area side opposite to the small area side on which the inlet fluid interface ports 14 are arranged.

In addition the device 1 has a vent 31 connected to the sample preparation chamber 10 via an insertion opening. The vent 31 is provided with means 19, 32 for blocking passage of liquid or solid particles to prevent contamination of a sample with dust, aerosols or the like and to prevent contamination of ambient with potentially dangerous sample material. These means comprise a filter material 32, preferably a porous material, which is placed in the vent 31. Alternatively or additionally the means may also comprise a tortuous section 19 a channel 13 which causes liquid or solid particles to adhere to curving channel walls so that such particles are thereby taken out of a gas flow. The tortuous section 19 is the more effective the more curves it comprises and the smaller their curving radii are. In the example shown the tortuous section 19 comprises only a single curve which suffices to provide a filtering effect.

The means 19, 32 for blocking passage of liquid or solid particles allow a gas exchange of the preparation chamber 10 with a surrounding atmosphere, usually air. In the device 1 shown a porous plastic material 32 is used to close the vent 31 which is placed on the back of the device 1.

The described disposable sample holding and processing device 1 is part of the handling kit 100 which also comprises the sample transfer tip 12 for transferring liquid into the disposable device. The handling kit 100 is shown in a back view in FIG. 5 and in a cross-section view along line CC of FIG. 5 in FIG. 6.

The sample transfer tip 12 is made of the same polymeric material as the body 2 of the disposable device 1, i.e. of polypropylene, although the sample transfer tip 12 could in principle also be made of a different material like glass. The disposable device 1 has a sample preparation chamber 10 with an insertion opening adapted to receive the sample transfer tip 12. The insertion opening and the sample transfer tip 12 are dimensioned in such a way that inserting the sample transfer tip 12 into the sample preparation chamber 10 causes a tight seal between an outer wall 40 of the sample transfer tip 12 and an inner wall 41 of the sample preparation chamber 10 The inner wall 41 of the sample preparation chamber 10 has a sealing area 46 which engages a sealing area 43 of the outer wall 40 of the sample transfer tip 12 to form the tight seal. The inner wall 41 and the sealing 43 of the sample preparation chamber 10 and the outer wall 40 of the sample transfer tip 12, between which the tight seal is formed, are circular. When the seal is in place the inner wall 41 of the sample preparation chamber 10 presses against the sample transfer tip 12. The outer diameter of the sample transfer tip 12 is typically in the range of 5 mm to 20 mm. In this way the sample transfer tip 12 can be used to pick up a sample from a blood collection tube or similar device where a sample may be stored.

Figure 6:
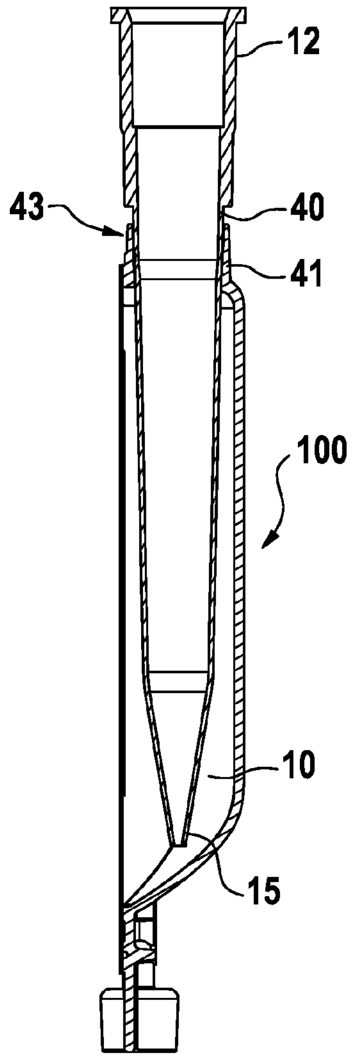
FIG. 6 shows a cross-section view of the FIG. 5 along the line CC.

The sample transfer tip 12 has an end 15 for insertion into an insertion opening of the sample preparation chamber 10. When the sample transfer tip 12 is introduced into the sample preparation chamber 10 as shown in FIG. 6 the end 15 of the sample transfer tip 12 is distanced from the insertion opening 16 (FIG. 1), i.e. its rim 11, by at least 1 cm, preferably at least 3 cm, especially at least 5 cm. Preferably, the distance between the end 15 of the sample transfer tip 12 an the sealing area 43 is larger than the immersion depth with which the sample transfer tip 12 is immersed in a sample liquid during a sample collection process when sample is taken from a sample reservoir, e.g. by aspiration.

After transfer of a sample to the sample preparation chamber 10 by means of the sample transfer tip 12, the tip 12 is friction locked in the device 1 by applying a suitable pushing force which pushes the tip 12 into its insertion position. This force is typically in the range of 2 N to 50 N, preferably between 5 N to 30 N. The friction lock between the sample transfer tip 12 in the insertion position and the disposable device creates a locking force of at least 2 N, preferably at least 5 N. Hence, a force of at least 2 N, preferably at least 5 N, would be necessary to pull the tip out of its insertion position. The sealing area 43 of the sample transfer tip 12 is provided as a frustum shaped section of the tip 12, but may easily be provided by different means.

The sample transfer tip 12 contains a plug 50 which is shown in FIG. 1 and made of a filter material, preferably a porous material. Fibrous materials, adsorptive materials, size exclusion materials and/or membranes may also be used. In the example shown the plug 50 is made of a porous plastic material. The plug 50 prevents contamination but is sufficiently permeable for air to communicate pressure and therefore allow sample aspiration and dosing as well as sip and spit mixing of sample liquid with reagents in the sample preparation chamber 10. The plug 50 filters aerosols from air which the device exchanges with a surrounding atmosphere.

Figure 5:
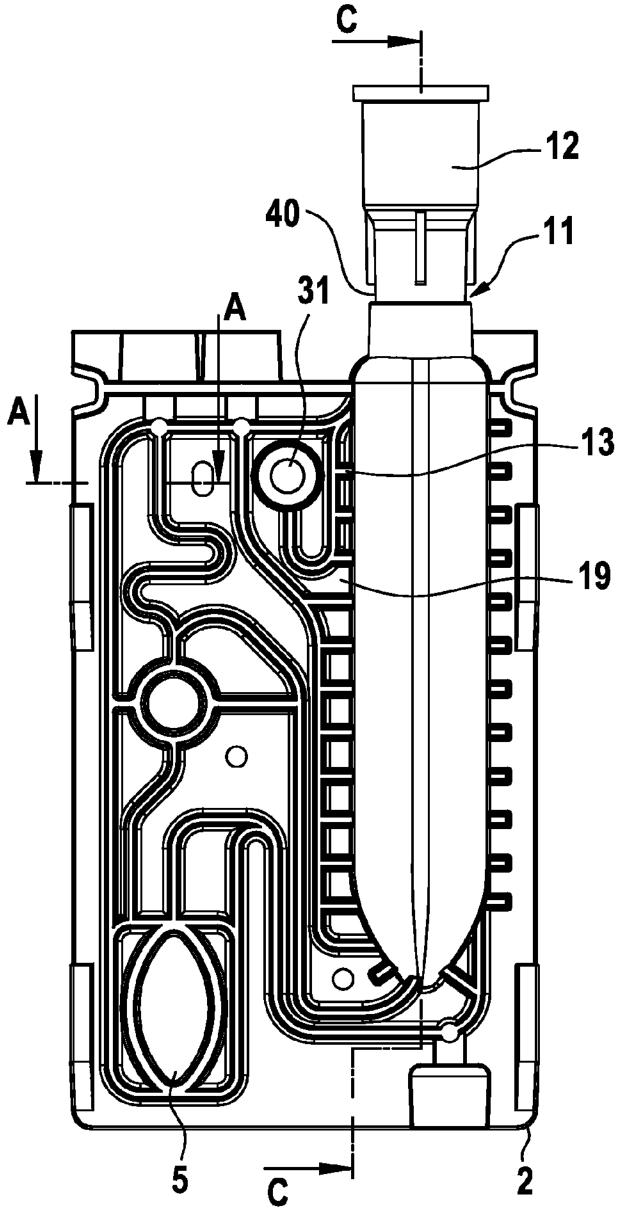
FIG. 5 shows a back view of the device body and inserted tip shown in FIG. 1.
Figure 7:
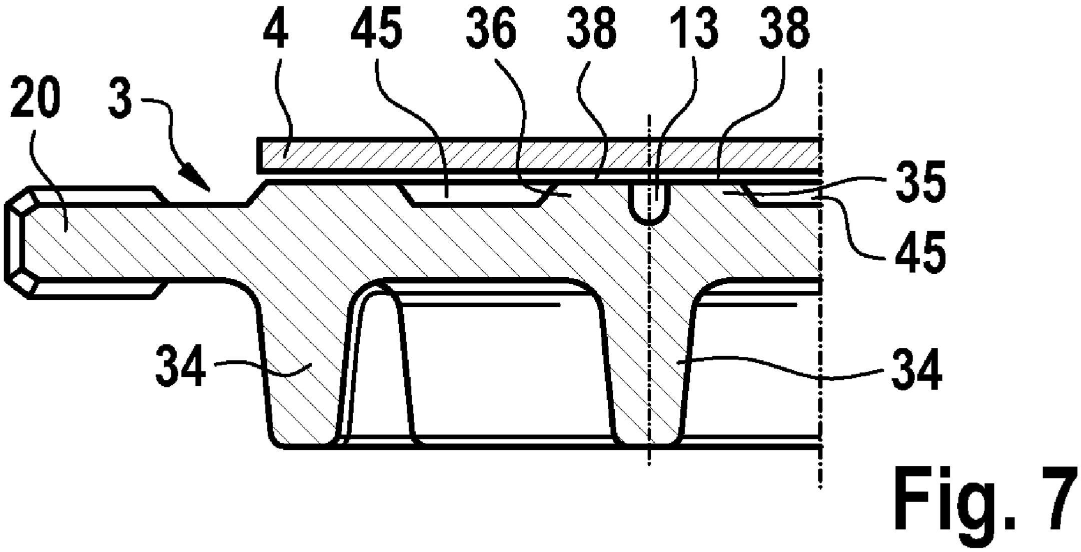
FIG. 7 shows a cross-section view of FIG. 4 along the line AA.

FIG. 7 shows a cross-section view along line AA of FIG. 5. As can be seen in FIG. 7 the sheet 20 carries at least one rib 34, 35, 36 for increasing the stiffness of the device body 2. The ribs 34, 35, 36 and the sheet 20 are manufactured as a single piece. In the device 1 shown ribs 34, 35, 36 are arranged both on the front side (i.e. on the structured surface 3 facing to the cover 4) of the sheet 20 and on the back side (the opposite side of the sheet 20 facing away of the sheet 20) of the sheet 20 for increased stiffness. Of course, a useful stiffening effect can also be achieved with ribs on either the front or back side of the sheet 20 only, or even by a single rib.

Figure 8:
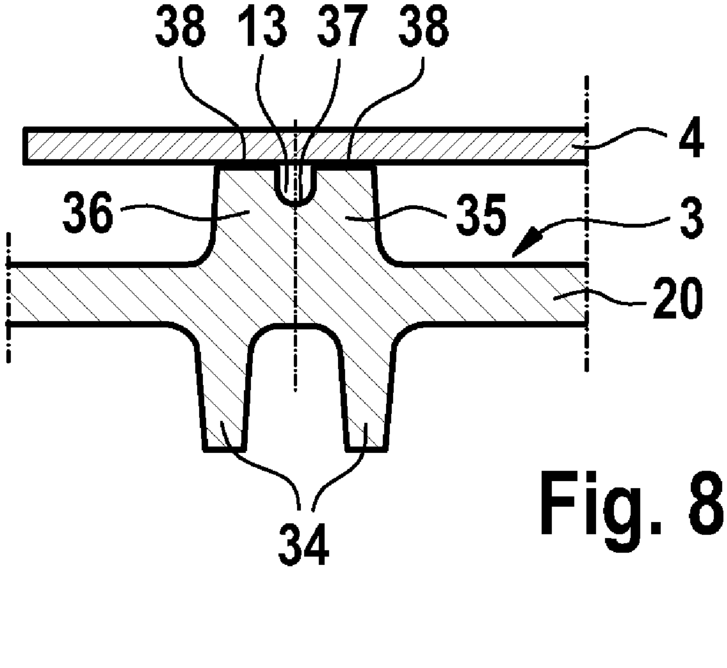
FIG. 8 shows a detail of another embodiment in a cross-section view corresponding to FIG. 7.

It is advantageous if at least one rib 35, 36 is arranged on the structured surface 3 such that at least one wall of a channel 6, 13 is formed by the rib. In the device 1 shown opposing walls of the channel 6 (or correspondingly of another channel 13), i.e. neighboring walls forming the channel 6 in between that walls, are formed by two corresponding ribs 35, 36 running parallel to each other. It is especially advantageous if the channel bottom 37 is elevated with respect to the surface of the sheet 20 adjacent to the ribs 35, 36, which form opposing walls of the channel 6, as shown in FIG. 8.

In similar fashion ribs 35, 36 or a raised section form sidewalls of the binding chamber 7 and the amplification chamber 5. The sealing cover 4 is fixed to the ribs 35, 36 on the front side of the sheet 20 and therefore touches the device body 2 only with a fraction of its surface area, which eases creation of a tight seal between the disposable body 2 and the sealing cover 4 and reduces bending of the device 1. As shown in FIGS. 7 and 8, ribs 35 and 36 have flat tops which are connected to the sealing cover 4. Thus pockets of air 45 exist between the sheet 20 and the cover 4. This provides for thermal insulation between the device body 2 and the sealing cover 4. At the same time an improved thermal connection between the sealing cover 4 and sample liquid is achieved as the sealing cover 4 forms a wall to the various channels 6, 13 and chambers 5, 7, 10 of the device 1.

The rib 34 or ribs on the back side of the sheet 20 are aligned with the inlet channel 6 or one or several other channels 13 on the front of the sheet 20 or with a chamber wall, no matter whether that channel 6, 13 or wall of a chamber 5, 7, 10 is straight or curved. Preferably the at least one rib 34 is parallel to a straight channel 6, 13 and/or to a straight portion of a channel 6, 13 and/or to a straight chamber wall. It is especially advantageous to arrange at least one the rib 34 or ribs on the back side of the sheet 20, i.e. on the side not covered by the sealing cover 4. Preferably, the at least one rib 34 is opposite of channels 6, 13 as shown in FIGS. 7 and 8 and/or the sealing area 38 in which the cover sheet 4 is connected to the device body 2. For additional stiffening further ribs may be added, especially on the back side of the sheet 20.

The sheet 20 has a thickness of 0.2 mm to 4 mm, especially 0.3 mm to 2 mm, preferably 0.5 mm to 1.5 mm, especially preferred of 0.8 mm to 1.0 mm. The ribs 34 on the back side of the sheet 20 have typically at half height a width which is 50% to 150% of the thickness of the sheet 20. The ribs 34 rise above the surface of the sheet 20 to a height which is 60% to 200%, preferably 80% to 150% of the thickness of the sheet 20. Ribs 35, 36 on the front side of the sheet 20 have a smaller height than ribs 34 on the back side of the sheet 20, i.e. ribs 35, 36 on the front side of the sheet 20 have preferably a height of 20% to 120% of the thickness of the sheet 20.

The differences in height between ribs 34 on the back side of the sheet 20 and ribs 35, 36 on its front side are largely due to differences in their function. Whereas ribs 34 serve only to increase the stiffness of the device body 2, ribs 35, 36 first and foremost serve to provide walls of one or several channels 6, 13 and/or to connect the device body 2 to the cover 4. Although the ribs 35, 36 are therefore much smaller in height they still provide a welcome stiffening effect.

REFERENCE NUMERALS

1 disposable sample holding and processing device
2 device body
3 structured surface
4 sealing cover
5 amplification chamber
6 inlet channel
7 binding chamber
8 solid phase adsorber
9 outlet of sample preparation chamber 10
10 sample preparation chamber
11 rim of insertion opening 16 of the sample preparation chamber 10
12 sample transfer tip
13 channels
14 interface port
14' interface port
15 end of the sample transfer tip 12
16 insertion opening of the sample preparation chamber
19 tortuous section of channel 13
20 sheet
21 fluid control area
22 fluid control area
23 fluidic system comprising channels 6, 13 and chambers 5, 7
29 septa
31 vent
32 filter material
34 rib (on back side of sheet 20)
35 rib (on front side of sheet 20)
36 rib (on front side of sheet 20)
37 channel bottom
40 outer wall of the sample transfer tip 12
41 inner wall of the sample preparation chamber 10
43 sealing area of tip
45 air pocket
46 sealing area of chamber
50 plug
100 handling kit

The invention claimed is:

1. A handling kit for analyzing a liquid sample by nucleic acid amplification comprising:

a disposable device adapted for holding and processing a sample for being used in an apparatus for analyzing a liquid sample, and a sample transfer tip for transferring liquid into the disposable device, wherein the disposable device has a sample preparation chamber which has an outlet and an insertion opening which is adapted to receive the sample transfer tip, the outlet being configured to be closed during sample preparation, the insertion opening of the sample preparation chamber and the sample transfer tip being dimensioned in such a way that inserting the sample transfer tip into an insertion position in the sample preparation chamber causes a seal between an outer wall of the sample transfer tip and an inner wall of the sample preparation chamber, such that the seal between the sample transfer tip and the inner wall of the of the sample preparation chamber prevents contamination of the sample and allows mixing of the liquid sample with reagents in the sample preparation chamber, the disposable device having a vent for venting the sample preparation chamber, wherein the vent is different from the outlet, the disposable device having a first channel which leads from the sample preparation chamber to the vent, the first channel comprising a first fluid control area comprising a closing apparatus configured to close the first channel and thereby control the flow of gases or liquids, and the disposable device having a second channel which leads from the outlet to a fluidic system, the second channel comprising a second fluid control area comprising a second closing apparatus configured to close the second channel and thereby control the flow of gases or liquids.

2. The handling kit according to claim 1, wherein the sample transfer tip has an end adapted for being introduced into the sample preparation chamber in such a way that the end is distanced from the insertion opening by at least about 1 cm after introduction.

3. The handling kit according to claim 1, wherein the sample transfer tip has an end adapted for being introduced into the sample preparation chamber in such a way that the end is distanced from the insertion opening after introduction by a distance which is at least about 30% of the total length of the sample transfer tip.

4. The handling kit according to claim 1, wherein the outer wall of the sample transfer tip forms the seal with a section of the inner wall of the sample preparation chamber which is distanced from the insertion opening of the sample preparation chamber.

5. The handling kit according to claim 1, wherein the sample transfer tip and the disposable device are adapted and dimensioned in such a way that the sample transfer tip is friction locked in an insertion position in the sample preparation chamber.

6. The handling kit according to claim 1, wherein the outer diameter of the sample transfer tip is in the range of about 5 mm to about 20 mm.

7. The handling kit according to claim 1, wherein the sample preparation chamber has a volume of about 50 μl to about 20 ml.

8. The handling kit according to claim 1, wherein the vent is provided with means for blocking passage of liquid or solid particles.

9. The handling kit according to claim 8, wherein the means for blocking passage of liquid or solid particles comprises a filter material which is placed in the vent.

10. The handling kit according to claim 1, wherein the sample transfer tip comprises a plug which filters aerosols from air which the device exchanges with a surrounding atmosphere, is made of a filter material, and prevents contamination and is permeable for air to communicate pressure and therefore allowing sample aspiration and dosing as well as sip and spit mixing of sample liquid with reagents in the sample preparation chamber.

11. The handling kit according to claim 10, wherein the disposable device comprises a device body and a cover which covers a structured surface of the disposable device body thereby forming a wall of the channel and of the chambers.

12. The handling kit according to claim 1, wherein the sample preparation chamber is connected by a channel to a fluid interface port for adding reagents into the sample preparation chamber.

13. The handling kit according to claim 1, wherein the disposable device comprises a system of channels and chambers which is connected to the outlet of the sample preparation chamber.

14. The handling kit according to claim 13, wherein an adsorber for binding nucleic acids is placed in the system of channels and chambers.

15. The handling kit according to claim 1, wherein:

the sample transfer tip has an end adapted for being introduced into the sample preparation chamber in such a way that the end is distanced from the insertion opening by at least about 5 cm after introduction, the sample transfer tip has an end adapted for being introduced into the sample preparation chamber in such a way that the end is distanced from the insertion opening after introduction by a distance which is at least about 75% of the total length of the sample transfer tip, the outer wall of the sample transfer tip forms the seal with a section of the inner wall of the sample preparation chamber which is distanced from the insertion opening of the sample preparation chamber by about 2 mm to about 10 mm, the sample transfer tip and the disposable device are adapted and dimensioned in such a way that the friction lock between the sample transfer tip in the insertion position and the disposable device creates a locking force of at least about 5 N, the inner wall of the sample preparation chamber has a sealing area which engages a sealing area of a section of the outer wall of the sample transfer tip to form the seal after introduction of the transfer tip into the sample preparation chamber, the sample transfer tip reaches with the major part of its length into the sample preparation chamber, the distance between the end of the sample transfer tip and the sealing area is larger than the immersion depth with which the sample transfer tip is immersed in a sample liquid during a sample collection process when sample is taken from a sample reservoir, the outer diameter of the sample transfer tip is in the range of about 5 mm to about 20 mm, and the sample preparation chamber has a volume of about 200 μl to about 10 ml.

* * * * *